United States Patent [19]

Schaub et al.

[11] Patent Number: 4,563,204

[45] Date of Patent: Jan. 7, 1986

[54] METHOD AND APPARATUS FOR WITHDRAWING A BOTTOM PRODUCT FROM A LOW-TEMPERATURE RECTIFYING COLUMN

[75] Inventors: Martin Schaub; Alexander Stucheli, both of Winterthur, Switzerland

[73] Assignee: Sulzer Brothers Limited, Winterthur, Switzerland

[21] Appl. No.: 556,319

[22] Filed: Nov. 30, 1983

[30] Foreign Application Priority Data

Dec. 3, 1982 [CH] Switzerland .......................... 7036/82

[51] Int. Cl.$^4$ ............................. B01D 3/42; F25J 3/02
[52] U.S. Cl. ............................................ 62/21; 62/32; 62/37; 203/2; 203/DIG. 18
[58] Field of Search ......................................... 203/1-3, 203/DIG. 18; 202/160, 205; 62/21, 37, 24, 32, 42; 208/DIG. 1; 196/132; 423/648 R, 648 A, DIG. 7

[56] References Cited

U.S. PATENT DOCUMENTS 3,238,111  3/1966  Harper .................................... 203/2

Primary Examiner—Frank Sever
Attorney, Agent, or Firm—Kenyon & Kenyon

[57] ABSTRACT

A quantity of tritium of less than 1 mol per hour is continuously withdrawn from the vaporization chamber of a low-temperature rectifying column by means of a withdrawal system.

The withdrawal system consists basically of two parallel-connected vacuum tanks which are alternately connected to the vaporization chamber via a withdrawal line containing a control valve. During operation, one of the vacuum tanks is connected to the low-temperature rectifying column and filled with tritium. As soon as one of the vacuum tanks has been filled with tritium, emptying of the tank starts while the second vacuum tank is connected to the vaporization chamber and similarly filled and then emptied.

8 Claims, 1 Drawing Figure

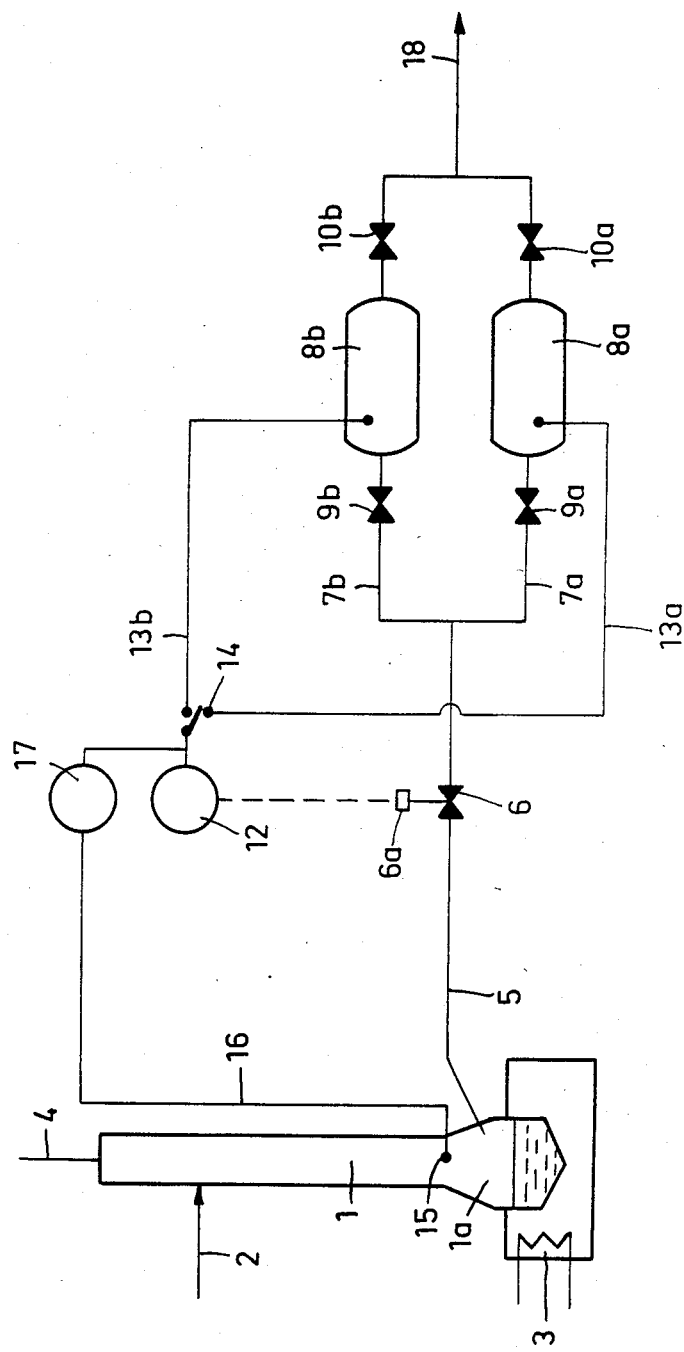

METHOD AND APPARATUS FOR WITHDRAWING A BOTTOM PRODUCT FROM A LOW-TEMPERATURE RECTIFYING COLUMN

This invention relates to a method and apparatus for withdrawing a bottom product in vapor form from a low temperature rectifying column. More particularly, this invention relates to a method and apparatus for withdrawing a bottom product at a rate of less than one mol per hour from a low temperature rectifying column.

Heretofore, various techniques have been used for the withdrawal of a bottom product from a low-temperature rectifying column. As is known, vaporized bottom product generally accumulates in relatively large quantitites within a vaporization chamber of a low-temperature rectifying column. In some cases, withdrawal of the vaporized bottom product has been performed by means of flow control or level control systems. However, the measuring instruments used in these systems have not been found to operate reliably for the withdrawal of extremely small quantities of bottom product, for example at a rate of less than one mol per hour on a continuous basis. Instead, the bottom product would be withdrawn on a discontinuous basis.

Generally, the basic disadvantages of a discontinuous withdrawal procedure are that the rectification is disturbed during the withdrawal period since the column gas loading varies temporarily, and, during the withdrawal phase, a product which still contains the top product, can be extracted from the column gas space.

Accordingly, it is an object of the invention to provide a method of withdrawing pure bottom product from a low-temperature rectifying column at a low rate without interfering with rectification.

It is another object of the invention to provide a relatively simple withdrawal system for continuously withdrawing bottom product from a vaporization chamber of a low-temperature rectifying column.

It is another object of the invention to withdraw a bottom product in continuous manner at a rate of less than one mol per hour.

Briefly, the invention provides a method and apparatus for the continuous withdrawal of a bottom product from a vaporization chamber of a low-temperature rectifying column.

The method is comprised of the steps of connecting a vacuum tank to the vaporization chamber in order to receive bottom product at ambient temperature and at a rate of less than one mol per hour, of controlling the amount of bottom product delivered to the tank in response to the pressure of the bottom product in the tank and of disconnecting the tank from the chamber at a time no later than when there is substantially a pressure equalization between the pressure in the tank and the pressure in the vaporization chamber. In this regard, the withdrawal flow from the vaporization chamber is proportional to the pressure in the vacuum tank since the product behaves as an ideal gas in the vacuum tank.

After disconnecting the tank, the bottom product is fed from the tank to a consumer within a time period shorter than the time period of filling of the tank. After emptying of the tank, the tank is again connected to the vaporization chamber for re-filling of the tank.

In addition to the low-temperature rectifying column, the apparatus of the invention includes a withdrawal system for continuously withdrawing the bottom product from the vaporization chamber of the column. This withdrawal system includes at least one vacuum tank, a first means connecting the tank to the vaporization chamber for withdrawing bottom product from the chamber to the tank at ambient temperature, a pressure controller connected to the tank to sense a pressure therein and connected to the first means for controlling the first means in response to a predetermined pressure in the tank and means connected to the tank for selectively emptying bottom product from the tank.

The withdrawal system may also include a pressure differential meter which is connected between and to the tank and the vaporization chamber in order to indicate a pressure differential therebetween.

In one embodiment, the withdrawal system includes a pair of vacuum tanks which are alternately connected to the vaporization chamber in parallel relation for a continuous withdrawal of bottom product from the chamber. In this case, the tanks are alternately filled and empty.

Apart from the recovery of pure bottom product, the rectifying column can be considerably reduced in size because of the continuous withdrawal of the operational contents of the vaporization chamber.

The dimensions of the volume of the vacuum tank are determined by the amount of bottom product withdrawn as well as the emptying time and accuracy of the pressure controller.

The method and apparatus may be particularly used in isotope separation processes, particularly, for the separation of tritium from a mixture containing hydrogen isotopes.

These and other objects and advantages of the invention will become more apparent from the following detailed description taken in conjunction with the accompanying drawing wherein:

The drawing illustrates a flow diagram of an apparatus constructed in accordance with the invention.

Referring to the drawing, the low-temperature rectifying column 1 may, for example, be constructed as a film column, a split tube column, or a packed column containing, for example a Raschig ring packing or packing elements of orderly structure. The important feature is that the column 1 should have a relatively small diameter, for example of one centimeter.

As indicated, the rectifying column 1 has a vaporization chamber at the lower end which is surrounded by a heating chamber 3. In addition, a supply line 2 is connected to the column 1 for feeding a mixture thereto while a top product line 4 is disposed at the top of column 1 for withdrawing top product. A reflux condenser is not shown since such does not contribute to an understanding of the invention.

In the present case, a mixture of deuterium (DT) and tritium ($T_2$) is fed to the column via the supply line 2 while tritium is to be continuously withdrawn as a bottom product from the vaporization chamber 1a and deuterium withdrawn as the top product through the line 4.

The column 1 cooperates with a withdrawal system for continuously withdrawing the bottom product from the chamber 1a. As indicated, the withdrawal system includes a pair of vacuum tanks 8a, 8b, means for selectively connecting each of the tanks 8a, 8b to the vaporization chamber 1a to alternately receive bottom product therefrom, a second means connected to the vacuum tanks for alternately emptying bottom product from each tank and a pressure controller 12.

The means for connecting the tanks 8a, 8b, to the vaporization chamber 1a includes a withdrawal line 5 which contains a control valve 6, a pair of branch lines 7a, 7b, which connect the withdrawal line 5 with the respective tanks 8a, 8b and change-over valves 9a, 9b in the respective branch lines 7a, 7b.

The means for emptying the vacuum tanks 8a, 8b includes a common withdrawal line 18 which is connected to the branch lines 7a, 7b in which the tanks 8a, 8b are disposed and a pair of change-over valves 10a, 10b which are disposed in a respective branch line 7a, 7b. The withdrawal line 18 leads to a suitable consumer (not shown). For example, the consumer may be an absorption apparatus constructed in known manner in which the tritium can be stored.

The pressure controller 12 is connected to the respective vacuum tanks 8a, 8b, via respective signal lines 13a, 13b and a selector 14 in order to receive a signal from the respective tank 8a, 8b representative of the pressure within the tank. In addition, the pressure controller 12 acts on a final control element 6a of the control valve 6 in order to control the flow of bottom product through the common withdrawal line 5.

In addition, a pressure differential meter 17 is connected via a line 16 to a pressure sensor 15 within the vaporization chamber 1a as well as the vacuum tanks 8a, 8b via the selector 14. The pressure differential meter 17 functions so as to indicate a pressure differential between a given vacuum tank 8a, 8b and the vaporization chamber 1a.

In operation, the withdrawal system is at ambient temperature. At the start of a withdrawal process, both vacuum tanks 8a, 8b are evacuated. Next, the change-over valve 9a is opened while the remaining valves 10a, 9b, 10b are closed. With the control valve 6 opened, the vacuum tank 8a begins to fill with tritium from the vaporization chamber 1a. During filling of the tank 8a, the pressure within the tank 8a is sensed and a corresponding signal is emitted over the line 13a and selector 14 to both the pressure controller 12 and the pressure differential meter 17. In response to the signal, the pressure controller 12 acts via the final control element 6a on the control valve 6 to open the valve 6 according to the amount of tritium to be withdrawn per unit of time. In this regard, the pressure in the vacuum tank 8a rises in proportion to the amount withdrawn from the vaporization chamber 1a. Thus, the control valve 6 is adjusted by the controller 12 depending upon the deviation of the pressure responsive signal in the circuit.

At a time no later than when the pressure in the vacuum tank 8a substantially corresponds to the pressure in the vaporization chamber 1a, as indicated by the meter 17, the valve 9a is closed. The valve 10a is then opened so that the contents of the vacuum tank 8a can be fed to the consumer via the line 18.

At the same time, the valve 9b is opened with the valve 10b remaining closed so that the vacuum tank 8b is now connected to the withdrawal line 5. In addition, the selector 14 is switched over so that the signal line 13b connects the vacuum tank 8b with the pressure controller 12 and pressure differential meter 17.

In a second period of time, which directly follows the first period of time, the vacuum tank 8b is filled with tritium from the column 1 in a similar manner. After the vacuum tank 8b has been filled, the previously evacuated vacuum tank 8a can be re-filled.

The frequency of the alternate filling and emptying of the vacuum tanks 8a, 8b is determined by the length of time during which one vacuum tank is in operation and the total time during which tritium is to be withdrawn.

Of note, various signal lines (not shown) and control means (not shown) are provided for the opening and closing of the respective change-over valves 9a, 9b; 10a, 10b in the proper sequence as indicated above. Likewise, the control means (not shown) is connected with the selector 14 to switch the selector from one signal line 13a, 13b to the other at the proper time.

As is known, tritium forms, for example, by neutron deposition in deuterium or heavy water or by ternary fusion in nuclear fusion reactors. For example, it is believed that future nuclear fusion reactors will use deuterium and/or tritium as fuel. Removal of tritium from the moderator and heat transport circuit of heavy water reactors is also necessary for radiotoxicological reasons. Special applictions may also require separation of tritium, for example from tritium-containing light water, from gas-cooled graphite-moderated nuclear reactors, liquid cooled light water and fast breader reactors, from industrial nuclear plants such as fuel rod reprocessing plants, and from tritium-containing hydrogen in waste gas or waste air plants in research and development laboratories which operate with tritium or in which tritium may form.

Tritium may also be used as a trace element for many applications, for example in the fluorescent material industry.

Hence, there are many applications in which tritium is to be isolated from a mixture for subsequent use.

A numerical example of a withdrawal process in the illustrated apparatus is indicated below with a numerical example of a discontinuous withdrawal process for comparison purposes.

CONTINUOUS WITHDRAWAL

Amount of tritium withdrawn:

$$2 \cdot 10^6 \text{ Ci/year} = 250 \text{ Ci/hour} = 0.0043 \text{ mol/hour}.$$

The gas loading at the bottom of the column 1 is 5 mol/hour.

DISCONTINUOUS PROCESS 0.043 mol of tritium to be withdrawn for 30 second time periods every 10 hours.

This would be equivalent to a withdrawal flow of:

$$(0.043 \cdot 3600/30) \text{ mol/hour} = 5.16 \text{ mol/hour}.$$

This shows that more product is withdrawn in discontinuous operation than the total gas loading in the rectification column. The consequence would be considerable interference with recitification and the withdrawal of impure product.

In the exemplified embodiment, each vacuum tank 8a, 8b is to be emptied every five hours.

The column pressure is 1.5 bar and the change-over from one vacuum tank to the other takes place at 1 bar. The vacuum tank size is $0.48 \cdot 10^{-3}$ cubic meters. The resulting pressure rise of 0.2 bar/hour can still be satisfactorily measured.

The invention thus provides a method and apparatus for continuously withdrawing a bottom product from a low-temperature rectifying column in a relatively simple and reliable manner. Further, the tritium can be removed at a rate which insures that only pure tritium is obtained. Likewise, rectification within the rectifying column can proceed without disturbance.

What is claimed is:

1. A method of withdrawing a bottom product from a vaporization chamber of a low-temperature rectifying column, said method comprising the steps of connecting a vacuum tank to the vaporization chamber to receive bottom product therefrom at ambient temperature;

controlling the amount of bottom product delivered to the tank in response to the pressure of the bottom product in the tank and at a rate of less than one mol per hour;

disconnecting the tank from the chamber at a time no later than when there is substantially a pressure equalization between the pressure in the tank and the pressure in the chamber;

thereafter feeding the bottom product in the tank to a consumer within a time period shorter than the time period of filling of the tank; and thereafter connecting the tank to the chamber for re-filling of the tank.

2. A method as set forth in claim 1 wherein a pair of vacuum tanks are alternately connected to the vaporization chamber in parallel relation for a continuous withdrawal of bottom product from the chamber and wherein the tanks are alternately filled and emptied.

3. In combination, a low-temperature rectifying column having a vaporization chamber for receiving a bottom product; and a withdrawal system for continuously withdrawing bottom product from said vaporization chamber, said system including at least one vacuum tank, first means connecting said tank to said chamber for withdrawing bottom product from said chamber to said tank at ambient temperature, a pressure controller connected to said tank to sense a pressure therein and connected to said first means for controlling said first means in response to a predetermined pressure in said tank, and second means connected to said tank for selectively emptying bottom product from said tank.

4. The combination as set forth in claim 3 wherein said withdrawal system includes a pressure differential meter connected between and to said tank and said chamber to indicate a pressure differential therebetween.

5. In combination, a low-temperature rectifying column having a vaporization chamber for receiving a bottom product; and a withdrawal system for continuously withdrawing bottom product from said vaporization chamber, said system including a pair of vacuum tanks, first means for selectively connecting each of said tanks to said chamber to alternately receive bottom product therefrom, second means connected to said vacuum tanks for alternately emptying bottom product from each tank, and a pressure controller selectively connected to each tank to sense a pressure therein and connected to said first means for controlling the flow of bottom product through said first means in response to the sensed pressure in a given tank.

6. The combination as set forth in claim 5 wherein said first means includes a withdrawal line connected to said chamber, a control valve in said line connected to said pressure controller, a pair of branch lines connected to said withdrawal line with each branch line connected to a respective tank and a pair of change-over valves, each said change-over valve being disposed in a respective branch line to open and close said respective branch line to a flow of bottom product.

7. The combination as set forth in claim 6 wherein said second means includes a common withdrawal line connected to said branch lines and a second pair of change-over valves, each said change-over valve of said second pair being disposed in a respective branch line downstream of a given tank to open and close said respective branch line to a flow of bottom product from a respective tank.

8. The combination as set forth in claim 5 wherein said withdrawal system includes a pressure differential meter connected to said chamber and selectively connected to said tanks to indicate a pressure differential between a given tank and said chamber.

* * * * *